US012797538B2

(12) United States Patent
Kaeufer et al.

(10) Patent No.: US 12,797,538 B2
(45) Date of Patent: Nov. 17, 2026

(54) METHOD, DEVICES AND MEDICAL DEVICE

(71) Applicant: B. Braun Melsungen AG, Melsungen (DE)

(72) Inventors: Guido Kaeufer, Horriwil (CH); Martin Schneider, Thun (CH); Mayur Suresh Dudhane, Schuepfheim (CH); Liesa Glaess, Schuepfheim (CH); Norbert Roth, Schuepfheim (CH); Robert Andree, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 629 days.

(21) Appl. No.: 18/362,233

(22) Filed: Jul. 31, 2023

(65) Prior Publication Data

US 2024/0033425 A1 Feb. 1, 2024

(30) Foreign Application Priority Data

Aug. 1, 2022 (DE) ..................... 10 2022 207 916.7

(51) Int. Cl.
*B32B 41/00* (2006.01)
*A61M 5/168* (2006.01)

(52) U.S. Cl.
CPC ..... *A61M 5/16813* (2013.01); *A61M 2207/00* (2013.01); *A61M 2207/10* (2013.01)

(58) Field of Classification Search
CPC .......... A61M 5/16813; A61M 2207/00; A61M 2207/10; A61M 2039/1072; A61M 39/18; A61M 39/22; A61M 39/26; A61M 2039/064; A61M 2039/1061; A61M 2039/2426; A61M 39/045
USPC .................... 156/60, 64, 350, 351, 378, 379
See application file for complete search history.

(56) References Cited

U.S. PATENT DOCUMENTS

| | | | |
|---|---|---|---|
| 6,673,178 B2 | 1/2004 | Ellner et al. |
| 2007/0012893 A1 | 1/2007 | Lee et al. |
| 2008/0161763 A1 | 7/2008 | Harding et al. |
| 2010/0030164 A1 | 2/2010 | Kimball et al. |
| 2011/0024664 A1 | 2/2011 | Burnard et al. |
| 2011/0046670 A1 | 2/2011 | Lehmann et al. |
| 2014/0194833 A1 | 7/2014 | Andrus |
| 2015/0266198 A1 | 9/2015 | Huber et al. |
| 2016/0228271 A1 | 8/2016 | Profit et al. |

FOREIGN PATENT DOCUMENTS

| | | | |
|---|---|---|---|
| CN | 109432589 A | 3/2019 |
| DE | 19902827 C1 | 6/2000 |
| DE | 102006020429 A1 | 10/2007 |
| DE | 102011104840 A1 | 12/2012 |
| DE | 102012223785 A1 | 6/2014 |
| EP | 4035635 A1 | 8/2022 |

*Primary Examiner* — Michael N Orlando
*Assistant Examiner* — Joshel Rivera
(74) *Attorney, Agent, or Firm* — Christopher A. Rothe; CM Law

(57) ABSTRACT

A method of producing an elastically deformable functional part for a medical device, devices for such methods, and a medical device having such a functional part. The functional part has an openable slit arrangement that widens or opens upon elastic deformation of the functional part and closes again in the absence of the deformation.

18 Claims, 2 Drawing Sheets

METHOD, DEVICES AND MEDICAL DEVICE

CROSS-REFERENCE TO RELATED APPLICATION(S)

This application claims priority under 35 U.S.C. § 119 to German Application No. 10 2022 207 916.7, filed on Aug. 1, 2022, the content of which is incorporated by reference herein in its entirety.

FIELD

The invention relates, in a first aspect, to a method of producing an elastically deformable functional part, especially functional part blank, for a medical device. In a second aspect, the invention relates to a further method of producing an elastically deformable functional part for a medical device. The invention further relates, in a third aspect, to a device for the production of an elastically deformable functional part, especially a functional part blank, for a medical device. The invention additionally relates, in a fourth aspect, to a further device for the production of an elastically deformable functional part for a medical device. The invention finally relates, in a fifth aspect, to such a medical device, especially a silicone valve device.

BACKGROUND

Gamma irradiation is a standard sterilization method for medical devices such as silicone valve devices. If the medical devices include radiation-crosslinkable material—for example silicone elastomers—these materials react under the action of high-energy radiation with crosslinking reactions. In the case of silicone valve devices in the form of slit valves, this can lead to unwanted closure of the slits, also referred to as healing.

In order to prevent such healing of slits, it is customary to add additives, called separating agents. The separating agents may be used in solid form, for example in the form of polymer particles. A disadvantage is that such additization generally leads to opaque materials. For many applications, for example connecting devices in the field of medical infusion therapy, however, maintenance of transparency of individual functional parts, for example valve bodies of slit valves, is absolutely necessary for proper use. It is also problematic that the addition of solid separating agents can cause fundamental changes to material properties.

Slits in such functional parts are typically created by severing a material of a blank for the functional part by means of a metal blade. But such a blade will undergo wear with time and will become correspondingly blunt. A worn, blunt blade has to be replaced by a sharp blade. This costs time and money.

As well as solid separating agents, liquid separating agents are also used. However, these must have sufficient wettability and, in particular, positional stability, in order to be able to exert their function, especially in a sustained manner.

Radiative sterilization, ageing processes and transport operations generally entail elevated temperatures, as a result of which the separating effect of liquid separating agents over time is frequently found to be too small. An additional factor is that some liquid separating agents, for example silicone oils, likewise react to radiative sterilization, which can additionally reduce the separating effect. The applying of such a separating agent on the slitted functional part is found to be challenging.

SUMMARY

It is therefore an object of the present invention to provide methods of producing an elastically deformable functional part for a medical device, devices for the production of such a functional part, and such a medical device, which have improved properties compared to conventional production methods and devices for such production methods and corresponding medical devices. In particular, particularly low-maintenance and consequently inexpensive production of such elastically deformable functional parts is to be enabled.

In a first aspect, the invention relates to a method of producing an elastically deformable functional part, especially functional part blank, for a medical device, wherein the functional part has an openable slit arrangement that widens or opens in the case of elastic deformation of the functional part and closes again in the absence of the deformation. The method comprises a step a), in which a blank for the functional part is provided, which includes an elastic, and especially transparent, material or consists of an elastic, and especially transparent, material. The method additionally comprises a step b), in which the material of the blank is severed at least in some regions, especially completely across a thickness, by means of ultrasound, so as to create at least one slit of the slit arrangement of the functional part. In the opened or widened state, the slit arrangement is preferably fluid-permeable. In the deformation-free, closed state of the slit arrangement, it is preferably fluid-tight. Advantageously, the use of ultrasound, it is possible to dispense with a blade for creation of the slit. Blades of this kind are subject to mechanical wear, which leads to blunting of such a blade over the service life. By means of ultrasound, it is possible to slit the material of the blank in a low-wear or even wear-free manner. It is thus possible firstly to save the costs for blade replacement, which is conventionally necessary on a recurring basis, and secondly also the time taken for a corresponding exchange of such a blade. Moreover, slit wall faces of a slit created by means of ultrasound have particularly good adhesion properties for any inhibitor material applicable to slit wall faces, which can inhibit or prevent self-healing of the material of the functional part.

The expression "functional part" in the context of the present invention shall be understood to mean a component or a component part or a component element of the medical device. In particular, such a functional part may be a valve body for a medical device designed as a silicone valve device, especially slit valve device.

The expression "medical device" in the context of the present invention shall especially be understood to mean a product for medical purposes such as a silicone valve device, preferably a slit valve device, for example for use in medical-technical or medical applications, for instance for the treatment of a patient.

The expression "slit wall faces" in the context of the present invention shall be understood to mean faces or surfaces of walls that form or define a slit or are involved in the forming of a slit.

The expression "separating agent" in the context of the present invention shall be understood to mean a substance or composition capable of reducing or even completely preventing closure, especially radiation-induced closure, of slits. "Closure" may be understood to mean crosslinking.

The expression "inhibitor material" is used here synonymously with "separating agent" in the context of the present invention.

The term "transparent" in the context of the present invention shall be understood to mean the ability of material to transmit electromagnetic waves having a wavelength of 380 nm to 780 nm (transmittance). In this respect, the term "transparent" shall be understood to mean "transparent to visible light". The transparency of the elastically deformable functional part is advantageously maintained at least partly, especially completely, even in the case of deformation. It is also conceivable that the material of the functional part is colored or tinted, such that it is transparent only to light having one or more colors, whereas light having different wavelengths cannot penetrate the material.

Appropriately, the slit arrangement comprises one or more slits. The slit arrangement may have two or more slits in a cross arrangement or star arrangement. Such a multitude of slits may be created simultaneously or successively. Such a slit may have a linear or curved shape.

In an embodiment of the method according to the first aspect of the invention, step b) comprises a substep b1), in which a sonotrode is activated, such that the sonotrode is set to oscillate with ultrasound frequency. The sonotrode may be fed by an ultrasound generator in order to be set in ultrasound oscillation. The ultrasound frequency may be 20 kHz to 40 kHz, preferably 30 kHz to 38 kHz. By means of such a sonotrode, the slit can be mounted in a particularly positionally accurate manner. It is thus possible to manufacture functional parts with particularly narrow tolerances, especially functional part blanks. The positionally accurate introduction of the slit can be promoted by precise guiding of the sonotrode, especially of an ultrasound unit comprising the sonotrode.

Appropriately, the activated sonotrode oscillates longitudinally and/or transversely to its extent, meaning that an amplitude of the ultrasound oscillation is measurable along and/or transverse to the extent of the sonotrode. The activated sonotrode preferably oscillates longitudinally and or transversely to the direction of the slit, i.e. an amplitude of the ultrasound oscillation is measurable along and/or transverse to the slit direction.

In a further embodiment of the method according to the first aspect of the invention, step b) comprises a substep b2), in which the sonotrode and/or the blank are moved relative to one another in a slit direction in order to sever the material of the blank at least in some regions and to create the at least one slit. Appropriately, the moving in substep b2) is at a feed rate of 0.02 m/s to 0.2 m/s, preferably 0.05 m/s to 0.15 m/s. The feed rate may be varied during the movement. The feed rate may be varied during the slitting or cutting operation for creation of the slit. In particular, the feed rate may be controlled by means of a closed-loop control circuit as a function of a cutting force that opposes the feed, such that the functional part is not deformed during the creation of the slit. In this way, the slit can be produced particularly accurately with regard to shape. In this way, moreover, it is possible to create a slit where any inhibitor material can adhere particularly well to the slit wall faces. In addition, in this way, it is possible to create a slit arrangement which is particularly fluid-tight in the deformation-free state. The functional part may be pretensioned in the mounted state, and this can decline as a result of creep characteristics with time.

In a further embodiment of the method according to the first aspect of the invention, step b) comprises a substep b3), in which the sonotrode is left in a predetermined final position for a predetermined dwell time when the sonotrode has reached the predetermined final position relative to the blank in the performance of substep b2). In this way, it is advantageously possible to prevent the still-fresh slit wall faces directly after creation thereof from being put back in a mutually opposite position, which would be conducive to self-healing. The dwell time may be 50 ms to 500 ms, preferably 80 ms to 300 ms. The sonotrode preferably penetrates the slit fully in the final position.

Appropriately, a cut quality in the creation of the slit can be influenced in a controlled manner via the choice of method parameters such as ultrasound frequency and/or feed rate and/or dwell time, especially in order to improve fluid-tightness of the slit arrangement and/or adhesion of any inhibitor material on the slit wall faces. The cut quality may express a variance of the shape of the slit created from a predetermined target shape.

In a further embodiment of the method according to the first aspect of the invention, the performance of step b) is concluded by deactivating the sonotrode such that the oscillation of the sonotrode is stopped. The sonotrode then thus ceases to oscillate. The sonotrode may be deactivated before, during or after the dwell time in the final position. The dwell time in the final position can ensure that the material of the functional part is fully severed. Conversely, the functional part can become unusable under some circumstances when the dwell time is too long.

Appropriately, the activated sonotrode oscillates at 50% to 100%, preferably 60% to 90%, of an amplitude output. Once the sonotrode is deactivated, no amplitude is measurable.

In a further embodiment of the method according to the first aspect of the invention, the method comprises an additional step c), in which the sonotrode and/or the slitted functional part are removed from one another. Preferably, the sonotrode has already been deactivated on removal in step c). In this way, it is advantageously possible to counteract self-healing or at least delay such self-healing. In addition, it is possible in this way to prevent slit wall faces of the slit created from being damaged in the removing of the sonotrode.

In a second aspect, the invention relates to a further method of producing an elastically deformable functional part for a medical device, wherein the functional part has an openable slit arrangement that widens or opens in the case of elastic deformation of the functional part and closes again in the absence of the deformation. The further method comprises a step A), in which a slitted functional part blank having a slit arrangement is provided, having at least one slit at which an elastic, and especially transparent, material of the functional part blank has been severed at least in some regions, preferably by means of ultrasound. The at least one slit has preferably been created by the method according to the first aspect of the invention as described above. In other words: the functional part blank used for the method according to the second aspect of the invention may be the functional part, especially functional part blank, produced by the method according to the first aspect of the invention. Accordingly, the methods according to the first two aspects of the invention may be conducted successively in a single procedure. The method according to the second aspect of the invention also comprises a step B) in which the slit arrangement is widened or opened. In addition, the method according to the second aspect of the invention includes a step C) in which at least one slit wall face of the slit arrangement of the functional part blank is provided at least in some regions, preferably over the full area, with an inhibitor material which inhibits or prevents self-healing of the material of the functional part blank, especially in the region of its slit arrangement. Appropriately, the providing of the slit wall face in step C) can be effected by coating or inoculating of the slit wall face in question. Preferably, two complementary, most preferably all, slit wall faces of the slit arrangement are provided with the inhibitor material. In this way, it is advantageously possible to assure openability of the slit arrangement, especially in a sustained manner. Since the slit of the functional part blank has been severed, preferably by means of ultrasound, the inhibitor material can adhere particularly well to the slit wall faces.

In one embodiment of the method according to the second aspect of the invention, step B) comprises a substep B1), in which the slitted functional part blank is clamped, especially by means of a clamp device. Step B) additionally comprises a substep B2), in which the functional part blank is deformed in order to open or widen the slit arrangement of the functional part blank. This advantageously improves the accessibility of the at least one slit wall face for the providing thereof with the inhibitor material.

In a further embodiment of the method according to the second aspect of the invention, prior to performance of substep B1) and/or of substep B2), the functional part blank is placed, especially without deformation, on a spike. Alternatively or additionally, during the performance of substep B2), the spike and/or the functional part blank are moved relative to one another, such that the functional part blank is deformed by means of the spike. Preferably, the spike for deforming the functional part blank presses along an axial extent of the spike against a region of the functional part blank in which the slit arrangement is present. The spike may thus press against the slit arrangement in order to widen or open it. The slit arrangement widened or opened by means of the spike may have a gaping slit, the slit wall faces of which are in an angled arrangement with respect to one another, such that the slit widens or opens away from the spike and narrows close to the spike. This results in particularly good accessibility of the at least one slit wall face for the providing thereof with the inhibitor material.

Appropriately, the spike is introduced into a hole in the functional part blank which is open at one end for the accommodation of the spike and closed at the other end by an integral membrane section of the functional part blank, where the slit arrangement is present in the membrane section. In this way, it is possible to match the deformation of the functional part blank particularly efficiently to the providing of the slit wall faces with the inhibitor material. In addition, the spike may serve as positioning aid for the alignment of the functional part blank, such that the inhibitor material can be provided with particular precision at the site intended. The spike may seal the slit arrangement in slit direction, in order to prevent inhibitor material from contaminating an inner face of the functional part and/or a device for the production of the functional part.

In a further embodiment of the method according to the second aspect of the invention, step C) comprises a substep C1), in which the functional part blank and a dosage unit for discharge of the inhibitor material are mutually converged until a predetermined target application distance has been attained. For this purpose, the functional part blank and/or the dosage unit may be moved relative to one another. The target application distance may be zero. The target application distance may be less than zero, meaning that the dosage unit in this case may project or be immersed into the slit arrangement. The target application distance may be −0.4 mm to +0.2 mm, preferably −0.2 mm to +0.1 mm. Step C) additionally comprises a substep C2), in which—once the target application distance has been attained—the inhibitor material is discharged in order to apply the inhibitor material at least in some regions, preferably over the full area, to the at least one slit wall face, preferably to two complementary, most preferably all, slit wall faces. It is thus possible to particularly effectively counteract self-healing.

In a further embodiment of the method according to the second aspect of the invention, the method comprises an additional step D), in which an excess volume of the inhibitor material is at least partly removed in order to separate the excess volume from an application volume of the inhibitor material that wets at least regions of the at least one slit wall face. The excess volume can be separated from the application volume by reversing a pumping direction or extrusion direction or conveying direction of the dosage unit and/or by moving it relative to the functional part blank. In this way, it is advantageously possible to achieve partial "withdrawal" of a discharged amount of the inhibitor material, especially of a bead of the inhibitor material. Alternatively or additionally, excess volume can be removed by dabbing or by means of a squeegee. In this way, it is possible to avoid or at least reduce unwanted soiling of apparatuses for conducting the method by the excess volume.

In a further embodiment of the method according to the second aspect of the invention, the method comprises a step E) which is conducted after step C) and in which the slit arrangement is closed via an elastic reset effect of the material of the functional part provided at least in some regions with the inhibitor material. The closing of the slit arrangement thus does not require any active measure or device.

Appropriately, the closing of the slit arrangement can distribute the inhibitor material over the slit wall faces, especially over the full area. The closing of the slit arrangement may be associated with cessation of the deformation.

In a further embodiment of the method according to the second aspect of the invention, for ejection of the functional part provided at least in some regions with the inhibitor material, after the performance of step E), the clamping of the functional part is released and the functional part is moved relative to the spike automatically as a result of the reset effect and/or by movement of the spike, especially relative to a clamp device for the clamping. As a result of the ejection, the functional part can remain loosely on the spike or slide off it completely. In the first case, it is advantageously possible to dispense with a separate ejection measure. In the second case, by contrast, it is possible to remove the functional part in a particularly controlled manner.

The steps and substeps of the method according to the first two aspects of the invention may be conducted in alphabetic and/or numeric sequence according to the above description. If viable, however, it is also possible to choose another sequence.

In a third aspect, the invention relates to a device for the production of an elastically deformable functional part, especially a functional part blank, for a medical device especially by a method according to the first aspect of the invention as described above. The device has a clamp device for clamping a blank for the functional part. In addition, the device has a sonotrode, especially one polished to high gloss, which, for creation of a slit of the slit arrangement, can be set to oscillate with an ultrasound frequency and can be moved relative to the clamp device. The above-detailed benefits of the method according to the first aspect of the invention can be exploited by means of the device, such that said benefits are also applicable mutatis mutandis to the device according to the third aspect of the invention.

In a fourth aspect, the invention relates to a further device for the production of an elastically deformable functional part for a medical device, especially by a method according to the second aspect of the invention as described above. The device has a clamp device for clamping a functional part blank. In addition, the device has a spike, where the clamp device and the spike are movable relative to one another for deformation-assisted opening or widening of the slit arrangement of the functional part blank. Moreover, the device has a dosage unit, preferably including an extruder and/or a dosage pump, for discharge of the inhibitor material that inhibits or prevents the self-healing of the material of the functional part blank, especially in the region of its slit arrangement, and for application, especially in regions or over the full area, of the inhibitor material to at least one, preferably to two complementary, most preferably to each, of the slit wall faces of the slit arrangement. The device according to the fourth aspect of the invention permits exploitation of the above-cited benefits of the method according to the second aspect of the invention, such that said benefits are also applicable mutatis mutandis to the device according to the fourth aspect of the invention.

In a fifth aspect, the invention relates to a medical device, especially silicone valve device, more preferably slit valve device, having at least one elastically deformable, and preferably transparent, functional part that has been produced by a method according to the first and/or second aspect of the invention and has an openable slit arrangement that widens or opens on elastic deformation of the functional part and closes again in the absence of the deformation, in order to control a fluid stream conducted through the medical device. The above-elucidated benefits of the first, second, third and fourth aspect of the invention are applicable mutatis mutandis to the medical device according to the fifth aspect of the invention.

Further benefits and features of the invention will be apparent from the following description of a preferred working example of the invention, which is illustrated by the drawings. In this context, identical reference numerals relate to identical or similar or functionally identical components.

It will be apparent that the features mentioned above and those still to be elucidated hereinafter are usable not just in the respective combination specified, but also in other combinations or on their own, without leaving the scope of the present invention.

DETAILED DESCRIPTION

Figure 1:
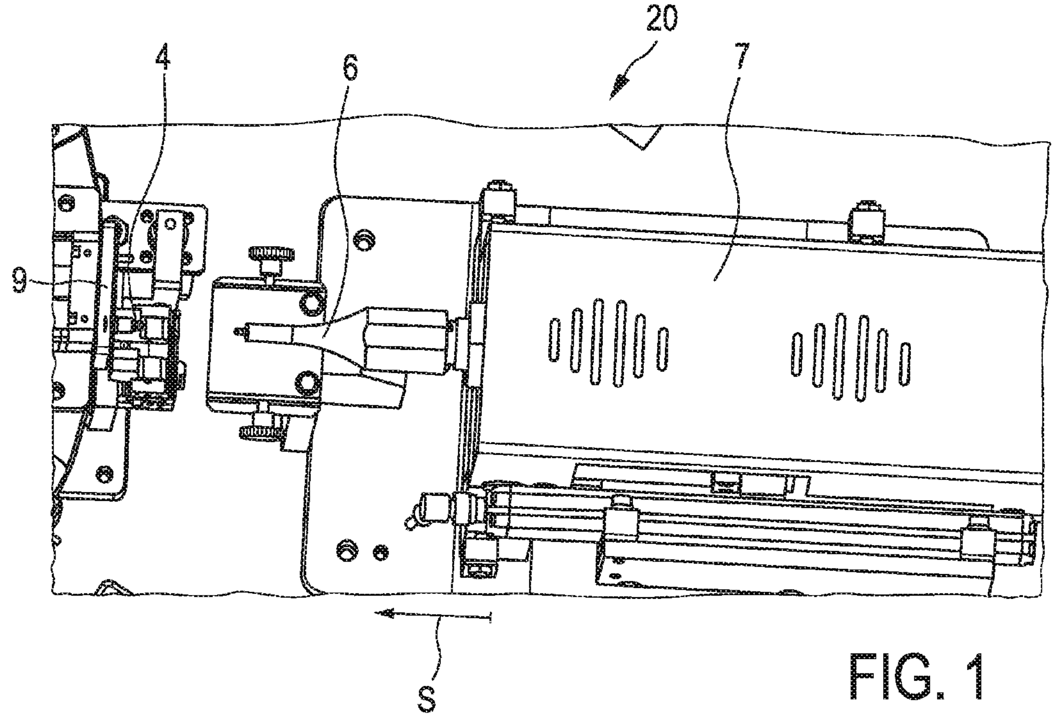
FIG. 1 shows, in a schematic perspective diagram, an embodiment of a device according to a third aspect of the invention for the production of an elastically deformable functional part for a medical device according to a fifth aspect of the invention during the performance of a method according to a first aspect of the invention.

FIG. 1 shows a schematic of one embodiment of a device 20 in a third aspect of the invention. The device 20 serves to produce an elastically deformable functional part 1 for a medical device 2 in a fifth aspect of the invention. In the present context, the device 20 serves to produce an elastically deformable functional part blank 1A.

The device 20 comprises a clamp device 9 for clamping a blank 4 for the functional part 1. In addition, the device 20 has a sonotrode 6. The sonotrode 6 can be set in oscillation with an ultrasound frequency by means of an ultrasound generator 7 of the device 20. The sonotrode 6 is movable relative to the clamp device 9. FIG. 1 shows the device 20 during the performance of a method V1 in a first aspect of the invention.

Figure 2:
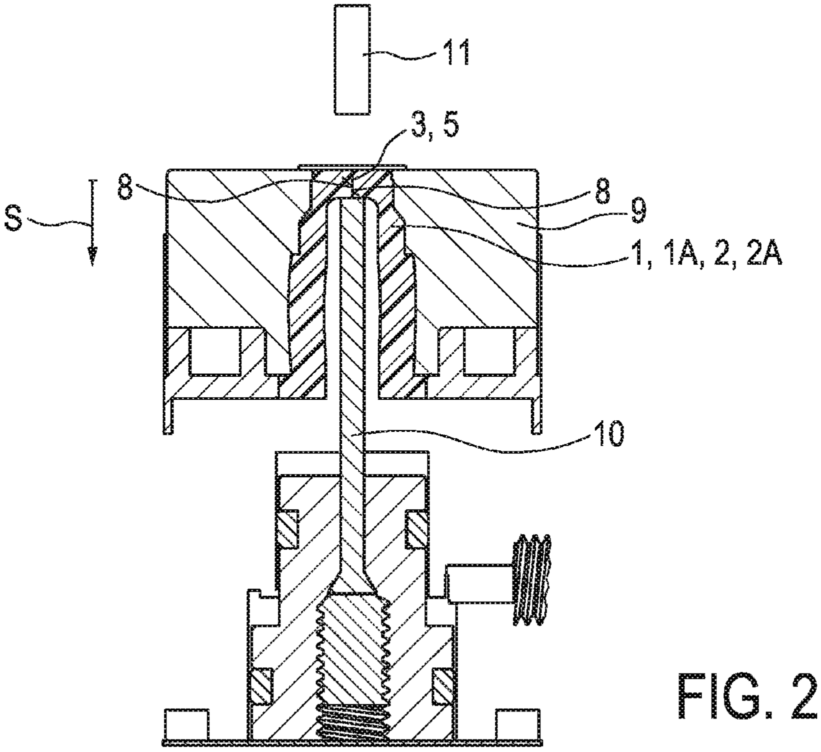
FIG. 2 shows, in a schematic cross-sectional diagram, an embodiment of a device according to a fourth aspect of the invention for the production of an elastically deformable functional part for the medical device according to the fifth aspect of the invention during the performance of a method according to a second aspect of the invention.

FIG. 2 shows a schematic of one embodiment of a device 30 in a fourth aspect of the invention. The device 30 serves to produce an elastically deformable functional part 1 for a medical device 2 according to the fifth aspect of the invention. The device 30 comprises a clamp device 9 for clamping a functional part blank 1A. The functional part blank 1A for the device 30 may be the functional part 1 that has been produced beforehand by means of the device 20 in method V1. In other words: the product of method V1 can be used in the form of a blank as one of the starting materials for a method V2 in a second aspect of the invention, during the performance of which the device 30 is shown in FIG. 2.

The device 30 has a spike 10. The spike 10 and the clamp device 9 are movable relative to one another. In addition, the device 30 comprises a dosage unit 11 for discharge of an inhibitor material. The inhibitor material inhibits or prevents the self-healing of a material of the functional part blank 1A. In particular, by means of the inhibitor material, self-healing in the region of a slit arrangement 3 of the functional part blank 1A can be inhibited or prevented. The dosage unit 11 may include an extruder and/or a dosage pump, by means of which the inhibitor material can be conveyed and dosed.

Figure 3:
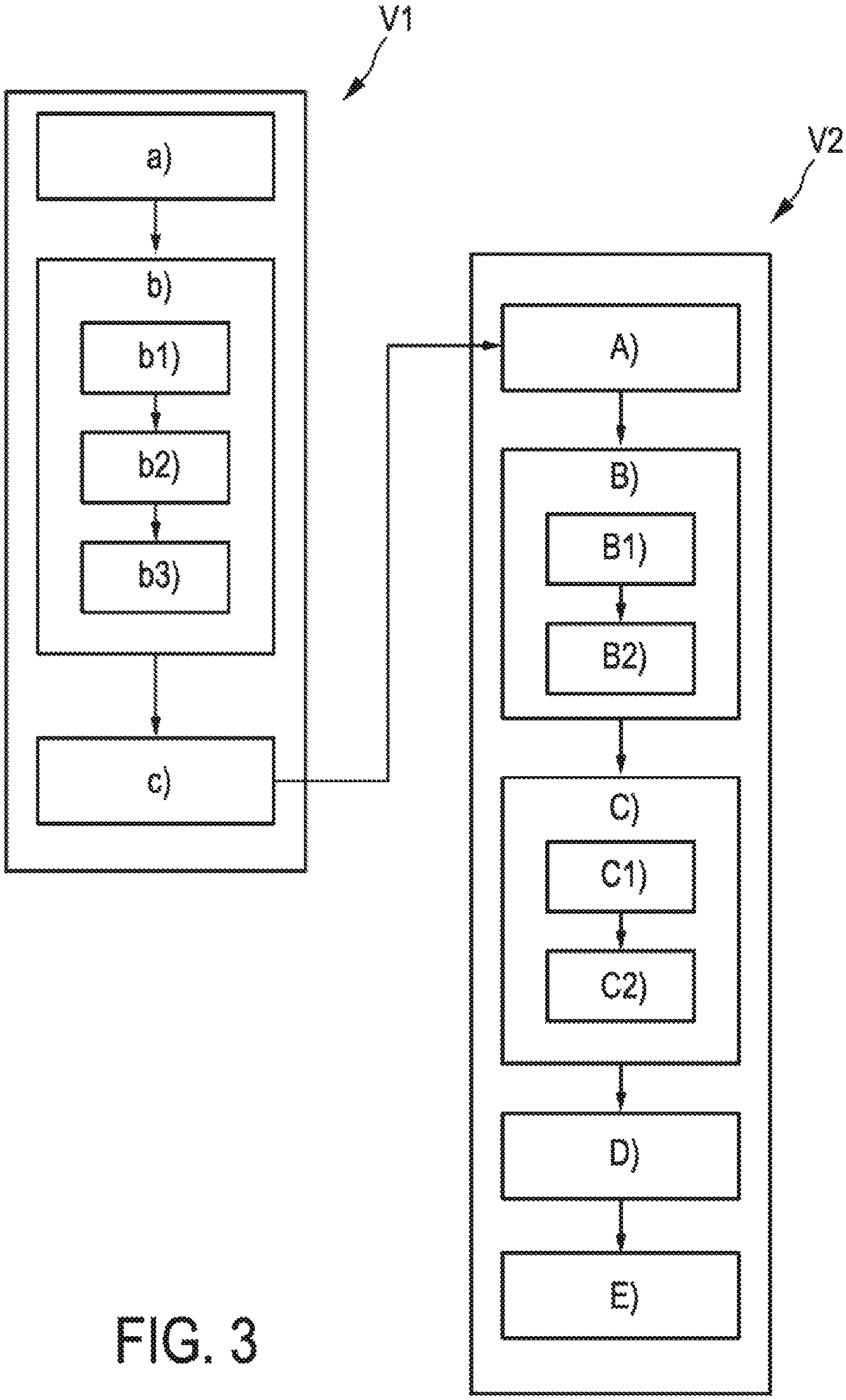
FIG. 3 shows a flow diagram for a procedure in which the methods according to the first two aspects of the invention for producing the elastically deformable functional part are combined with one another.

FIG. 3 shows a schematic or flow diagram of a procedure in the case of performance of the two methods V1, V2 in succession. The procedure can thus itself be regarded as a combined method comprising the two methods V1, V2 as successive steps, and by means of which the elastically deformable functional part 1 can be produced.

The method V1 serves to produce an elastically deformable functional part 1 for a medical device 2. The functional part 1 produced by the method V1 may be used as functional part blank 1A for the method V2. The functional part 1 has an openable slit arrangement 3. The slit arrangement 3 widens on elastic deformation of the functional part 1 or opens on elastic deformation of the functional part 1. In the absence of deformation, the slit arrangement 3 closes again. As already addressed, the elastically deformable functional part 1 to be produced by method V1 may serve as functional part blank 1A, which is then processed further by method V2 in order to complete the functional part 1. The aforementioned properties of the functional part 1 produced by method V1 consequently also exist in the case of functional part blank 1A for method V2.

The method V1 comprises a step a), in which a blank 4 for the functional part 1 is provided. The blank 4 includes an elastic material. This material may be transparent. The blank 4 may consist of the elastic, and especially transparent, material. The method V1 also includes a step b), in which the material of the blank 4 is severed at least in some regions. The material of the blank 4 is severed in step b) by means of ultrasound, such that at least one slit 5 of the slit arrangement 3 of the functional part 1 is created. The slit arrangement 3 may comprise multiple slits 5. Such a plurality of slits 5 may, for example, be in a cross arrangement or star arrangement. The at least one slit 5 may be of linear or curved shape.

The material of the blank 4 may include an elastomer or consist of an elastomer. The elastomer is preferably a thermoplastic elastomer. The elastomer may especially be selected from a group consisting of silicone elastomer, silicone rubber, acrylonitrile-butadiene rubber, hydrogenated acrylonitrile-butadiene rubber, styrene-butadiene rubber and mixtures of at least two of the aforementioned elastomers. Alternatively or in combination, the material of the blank 4 may be another polymer which is crosslinkable or where crosslinking reactions are predominant.

According to FIG. 3, step b) of method V1 comprises a substep b1). In substep b1), the sonotrode 6 is activated, such that it is set in oscillation with ultrasound frequency. The ultrasound frequency may be 20 kHz to 40 kHz, preferably 30 kHz to 38 kHz. The ultrasound frequency preferably corresponds to a resonance frequency of the sonotrode 6.

The sonotrode 6 may have been polished to high gloss. The sonotrode 6 may have been formed with or from a metallic material, especially an alloy comprising iron and/or titanium and/or aluminum. The sonotrode 6, as apparent in FIG. 1, is fed by an ultrasound generator 7. The ultrasound generator 7, in substep b1), sets the sonotrode 6 in oscillation with ultrasound frequency. According to FIG. 3, step b) of method V1 additionally comprises a substep b2). In substep b2), the sonotrode 6 and/or the blank 4 are moved relative to one another in a slit direction S. As a result of the movement in substep b2), the material of the blank 4 is severed at least in some regions, in order to create the at least one slit 5. The movement in substep b2) may be at a feed rate of 0.02 m/s to 0.2 m/s, preferably 0.05 to 0.15 m/s.

Step b) of method V1, according to FIG. 3, also includes a substep b3). In substep b3), the sonotrode 6 dwells in a predetermined final position for a predetermined dwell time when the sonotrode 6 has reached the predetermined final position relative to the blank 4 in the performance of substep b2). In the final position, the sonotrode 6 may fully penetrate the slit 5. For example, the sonotrode 6 in its final position fully penetrates the slit 5 in the slit direction S. The dwell time may be 50 ms to 500 ms, preferably 80 ms to 300 ms.

A cut quality of the slit 5 created which is achievable by the severing of the material of the blank 4 at least in regions in step b) can be influenced in a controlled manner by method parameters such as the chosen ultrasound frequency of the sonotrode 6, the feed rate and the dwell time. The cut quality can be influenced correspondingly in order to improve a fluid-tightness of the slit arrangement 3. In addition, controlled influencing of the cut quality can improve adhesion of the inhibitor material, which inhibits or prevents self-healing of the material of the functional part 1, 1A, especially in the region of its slit arrangement 3. By adjusting the method parameters, it is advantageously possible to influence roughness of slit wall faces 8 of the slit 5 in a controlled manner.

When the sonotrode 6 is activated, it is set in ultrasound oscillation with an amplitude. If the sonotrode 6 is deactivated, there is no amplitude. The activated sonotrode 6 may oscillate at 50% to 100%, preferably 60% to 90%, of its amplitude power.

For example, for conclusion of the performance of step b) of method V1, the sonotrode 6 is deactivated, and so the oscillation of the sonotrode 6 is stopped. As a result of the deactivating of the sonotrode 6, the sonotrode 6 can thus cease to oscillate.

Method V1, according to FIG. 3, additionally comprises an additional step c), in which the sonotrode 6 and/or the slitted functional part 1 are removed from one another. The deactivating of the sonotrode 6 may be undertaken before, during or after the dwell time in the final position. The sonotrode 6 has preferably already been deactivated on removal in step c).

As already mentioned, FIG. 3 additionally shows the sequence of a method V2 in a further aspect of the invention. Method V2 serves to produce an elastically deformable functional part 1 for the medical device 2 in the fifth aspect of the invention. The functional part 1 has an openable slit arrangement 3 which widens or opens on elastic deformation of the functional part 1 and which closes again in the absence of the deformation. Method V2 includes a step A) in which a slitted functional part blank 1A is provided.

The functional part blank 1A has been produced, for example, by the above-described method V1. The functional part blank 1A in the present context is thus—as already mentioned above—for example, the functional part 1 produced by method V1. The functional part blank 1A accordingly has a slit arrangement 3 comprising at least one slit 5. An elastic, and especially transparent, material of the functional part blank 1A is severed at least in some regions at the at least one slit 5. The at least one slit 5 has been created, for example, in step b) of method V1.

Method V2 also comprises a step B). In step B), the slit arrangement 3 of the functional part blank 1A is widened or opened. In addition, method V2 has a step C) in which at least one slit wall face 8 of the slit arrangement 3 of the functional part blank 1A is provided with the inhibitor material. The inhibitor material inhibits or prevents self-healing of the material of the functional part blank 1A, especially in the region of its slit arrangement 3. The providing of the slit wall face 8 can be effected by coating or inoculating with the inhibitor material. For example, two complementary slit wall faces 8 of the slit arrangement 3 that collectively bound the at least one slit 5 are provided with the inhibitor material. Preferably, all slit wall faces 8 of the slit arrangement 3 are provided with the inhibitor material.

For a transition between method V1 and method V2, the functional part blank 1A may be moved from a clamp device 9 of the device 20 to a clamp device 9 of the device 30. Alternatively, it is also conceivable that one and the same clamp device 9 is used, when the devices 20, 30 are provided in a common installation. When the functional part blank is transferred between the clamp devices 9 of the devices 20, 30, an alignment of the slit arrangement 3 is preferably maintained.

The inhibitor material may include an oil. For example, the oil may be selected from the group consisting of silicone oil, alkylated naphthalene (AN), chlorotrifluoroethylene (CTFE), ester oil, mineral oil, especially synthetic mineral oil, polyalkylated cyclopentane (MAC), polyalphaolefin (PAO), polyphenyl ether (PPE), polyglycol oil (PG), perfluorinated polyether oil (PFPE), triglycerides and mixtures of at least two of the aforementioned oils. The oil may especially be a fluorinated silicone oil.

The inhibitor material may additionally include a thickener. The thickener may be selected from the group consisting of aluminum soap, aluminum complex soap, barium soap, barium complex soap, calcium soap, calcium complex soap, lithium soap, lithium complex soap, sodium soap, sodium complex soap, polytetrafluoroethylene (PTFE), inorganic thickener, especially bentonite, polyurea, silica and mixtures of at least two of the aforementioned thickeners.

The inhibitor material may also include a solid which is not a thickener, where the solid is especially selected from the group consisting of salts, saccharides, vitamins and mixtures of at least two of the aforementioned solids.

The inhibitor material may be liquid. The inhibitor material may be viscous or in paste form. The inhibitor material may be thixotropic or anti-thixotropic.

According to FIG. 3, step B) of method V2 comprises a substep B1). In substep B1), the slitted functional part blank 1A is clamped. For example, the slitted functional part blank 1A is clamped by means of a clamp device 9 assigned to the device 30. Step B) in the present context also comprises a substep B2) in which the functional part blank 1A is deformed. As a result of the deforming of the functional part blank 1A in substep B2), the slit arrangement 3 of the functional part blank 1A is opened or widened.

Before the performance of substep B1) and/or of substep B2), the functional part blank 1A may be placed on a spike 10. This is shown in FIG. 2 in the manner of a snapshot. For example, the functional part blank 1A may be placed on the spike 10 without deformation. During the performance of substep B2)—i.e. in the deforming of the functional part blank 1A—the spike 10 and/or the functional part blank 1A may be moved relative to one another, such that the functional part blank 1A is deformed by means of the spike 10. The spike 10 can be introduced into a hole in the functional part blank 1A. This hole, as apparent in FIG. 2, may be open at one end and closed at the other end by an integral membrane section of the functional part blank 1A. The slit arrangement 3 may be present here at the membrane section. The spike 10 can act on the membrane section in the slit direction S. In this way, the slit arrangement 3 may be pressed on as a result of the deformation of the functional part blank 1A. The slit arrangement 3 may gape open as a result of the deforming.

Step C) of method V2, according to FIG. 3 comprises a substep C1). In substep C1), the functional part blank 1A and a dosage unit 11 are mutually converged. The dosage unit 11 may be assigned to the device 30; cf. FIG. 2. The dosage unit 11 serves to discharge the inhibitor material. The mutual convergence in substep C1) is effected until a predetermined target application distance is attained. The mutual convergence in substep C1) can be effected by movement of functional part blank 1A and/or dosage unit 11 relative to one another. The target application distance may be zero. The target application distance may be less than zero, meaning that the dosage unit 11 in this case may project partially into the slit arrangement 3. The target application distance may be −0.4 mm to +0.2 mm, preferably −0.2 mm to +0.1 mm.

Step C) comprises, for example, a further substep C2). In substep C2), once the target application distance has been attained, the inhibitor material is discharged in order to apply the inhibitor material at least to regions of the at least one of the slit wall faces 8. Preferably, the inhibitor material is applied over the full area of the at least one slit wall face 8. For example, the inhibitor material may be applied to two complementary slit wall faces 8 that collectively bound the slit 5 of the slit arrangement 3. The inhibitor material may be applied in substep C2) to each of the slit wall faces 8 of the slit arrangement 3.

According to FIG. 3, method V2 also comprises an additional step D). In step D), an excess volume of the inhibitor material is at least partly removed. This involves removing the excess volume from an application volume of the inhibitor material that wets at least regions of the at least one slit wall face 8. The at least partial removal of the excess volume of the inhibitor material in step D) can be effected, for example, by reversing a pumping direction or extrusion direction or conveying direction of the dosage unit 11. Alternatively or additionally, the dosage unit may be moved relative to the functional part blank to remove the excess volume. In this way, it is possible to achieve at least partial "withdrawal" of a discharged amount of the inhibitor material. For example, a discharged bead of the inhibitor material may be partly withdrawn. Alternatively or additionally, excess volume of the inhibitor material can be removed by dabbing or by means of a squeegee. In order to remove the excess volume by means of the squeegee, this may be moved along an extent of the at least one slit 5 relative to the functional part 1.

By means of a camera, it is possible to visually monitor a geometry of the slit arrangement 3 and/or a desirably complete wetting of the at least one slit wall face 8.

Method V2, according to FIG. 3, also comprises an additional step E) which is performed after step C). In step E), the slit arrangement 3 is closed as a result of an elastic reset effect of the material of the coated functional part 1. The closing in step E) can result in distribution of the inhibitor material over the slit wall faces 8. The closing of the slit arrangement 3, by virtue of the elastic reset effect, is associated with loss of deformation.

For example, in order to eject the functional part 1 provided with the inhibitor material at least in regions, after the performance of step E), the clamping of the functional part 1 is released. The functional part 1 is then moved relative to the spike 10 automatically as a result of the reset effect. Alternatively or additionally, the functional part 1 is moved by moving the spike 10, especially relative to the clamp device 9. Thereafter, the finished functional part 1 may be removed. The spike 10, after removal of the functional part 1, may be returned to its original position such that it is available for another performance of method V2. The finished functional part 1 can be removed by ejection from the device 30.

The sonotrode 6 of the device 20 can be set in oscillation with ultrasound frequency in order to create the at least one slit 5 of the slit arrangement 3.

The spike 10 of the device 30 serves for deformation-assisted opening or widening of the slit arrangement 3 of the functional part blank 1A. The dosage unit 11 for discharge of the inhibitor material of the device 30 serves for application, especially in some regions or over the full area, of the inhibitor material on at least one, preferably on two complementary, most preferably of each, of the slit wall faces 8 of the slit arrangement 3.

The functional part 1 that can be seen in FIG. 2 is part of a medical device 2 according to the fifth aspect of the invention. For example, the medical device 2 may be a silicone valve device 2A. The silicone valve device 2A may be designed as a slit valve device. The deformation-assisted widening or opening and closing of the functional part 1 may be controlled by a fluid stream conducted through the medical device 2.

The functional part 1 produced by method V1, which can be used as functional part blank 1A for method V2, differs from the functional part 1 produced by means of method V2 exclusively in that, in the case of the latter, the at least one slit wall face 8 has been provided with the inhibitor material.

The medical device 2 may be used as connecting device of a medical infusion system or for a medical infusion system. Accordingly, the medical device 2 or the silicone valve device 2A may be configured as a three-way tap. Alternatively, the medical device 2 or the silicone valve device 2A may be configured as a one-way or two-way tap or as a manifold, i.e. as a unit or system comprising or composed of a series, i.e. a succession, of one one-way taps. The functional part 1, 1A of the medical device 2 may form a valve body of the medical device 2. The valve body may be cup- or bell-shaped. A base of the cup- or bell-shaped valve body may be formed by an integral membrane section with the slit arrangement 3 disposed thereon. The valve body may be in one-piece form. The slit walls 8 adjoin one another, for example, in a deformation-free state of the valve body, such that a fluid pathway leading through the medical device 2 is closed in a fluid-tight manner. In the case of deformation-assisted widening or opening of the slit arrangement 3, this fluid pathway is opened, such that a fluid can flow along it through the slit arrangement 3. For example, the slit arrangement may be widened or opened in that a connection component is connected in a fluid-conducting manner to the medical device 2 with deformation of the functional part 1, and to the fluid pathway conducted through the medical device 2.

The invention claimed is:

1. A method of producing an elastically deformable functional part for a medical device, wherein the functional part has an openable slit arrangement that widens or opens in the case of elastic deformation of the functional part and closes again in the absence of the deformation, the method comprising the following steps:

a) providing a functional part blank having a slit arrangement with at least one slit at which an elastic material of the functional part blank has been severed at least in some regions by ultrasound;

b) widening or opening the slit arrangement; and c) providing at least one slit wall face of the slit arrangement of the functional part blank at least in some regions with an inhibitor material which inhibits or prevents self-healing of the material of the functional part blank.

2. The method according to claim 1, wherein a) the functional part blank includes an elastic material or consists of an elastic material.

3. The method according to claim 1, comprising severing the functional part blank by activating a sonotrode, such that the sonotrode is set to oscillate with ultrasound frequency.

4. The method according to claim 3, wherein severing the functional part blank further comprises moving the sonotrode and/or the blank relative to one another in a slit direction in order to sever the material of the blank at least in some regions and to create the at least one slit.

5. The method according to claim 4, wherein severing the functional part blank further comprises leaving the sonotrode in a predetermined final position for a predetermined dwell time when the sonotrode has reached the predetermined final position relative to the blank in the performance of moving the sonotrode and/or the blank relative to one another in the slit direction.

6. The method according to claim 3, wherein severing the functional part blank is concluded by deactivating the sonotrode such that the oscillation of the sonotrode is stopped.

7. The method according to claim 3, further comprising c) removing the sonotrode and the functional part blank from one another.

8. The method according to claim 1, wherein step B) comprises the following substeps:

b1) clamping the functional part blank; and b2) deforming the functional part blank in order to open or widen the slit arrangement of the functional part blank.

9. The method according to claim 8, wherein prior to performance of substep B1) and/or of substep B2), the functional part blank is placed on a spike, and/or in that, during the performance of substep B2), the spike and/or the functional part blank are moved relative to one another, such that the functional part blank is deformed by means of the spike.

10. The method according to claim 1, wherein step C) comprises the following substeps:

c1) mutually converging the functional part blank and a dosage unit for discharge of the inhibitor material until a predetermined target application distance has been attained, c2) once the target application distance has been attained: discharging the inhibitor material in order to apply the inhibitor material to the at least one slit wall face at least in some regions.

11. The method according to claim 1, wherein the method comprises the following additional step:

d) at least partly removing an excess volume of the inhibitor material in order to separate the excess volume from an application volume of the inhibitor material that wets at least regions of the at least one slit wall face.

12. The method according to claim 9, wherein the method comprises the following additional step which is conducted after step c):

e) closing the slit arrangement via an elastic reset effect of the material of the functional part provided at least in some regions with the inhibitor material.

13. The method according to claim 12, wherein, for ejection of the functional part, after the performance of step e), the clamping of the functional part is released and the functional part is moved relative to the spike automatically as a result of the reset effect and/or by movement of the spike.

14. A device for the production of an elastically deformable functional part for a medical device by a method according to claim 1, the device comprising:

a clamp device for clamping the functional part blank; and a sonotrode which, for the creation of a slit of the slit arrangement, can be set to oscillate with an ultrasound frequency and can be moved relative to the clamp device.

15. A device for the production of an elastically deformable functional part for a medical device by a method according to claim 1, the device comprising:

a clamp device for clamping the functional part blank;

a spike, where the clamp device and the spike are movable relative to one another for deformation-assisted opening or widening of the slit arrangement of the functional part blank; and a dosage unit for discharge of the inhibitor material that inhibits or prevents the self-healing of the material of the functional part blank, and for application of the inhibitor material to at least one of the slit wall faces of the slit arrangement.

16. A medical device comprising at least one elastically deformable functional part produced by the method according to claim 1, the medical device having an openable slit arrangement that widens or opens upon elastic deformation of the functional part and closes in the absence of deformation to control a fluid stream conducted through the medical device.

17. The method according to claim 1, wherein at least one of:

the elastic material of the functional part blank is transparent; and the inhibitor material inhibits or prevents self-healing of the material of the functional part blank in a region of the slit arrangement.

18. The method according to claim 12, wherein, for ejection of the functional part, after the performance of step e), the clamping of the functional part is released and the functional part is moved relative to the spike automatically as a result of the elastic reset effect and/or by movement of the spike relative to a clamp device for the clamping.

* * * * *